United States Patent
Hayashizaki (12)

(10) Patent No.: US 6,294,337 B1
(45) Date of Patent: Sep. 25, 2001

(54) METHOD FOR DETERMINING DNA NUCLEOTIDE SEQUENCE

(75) Inventor: Yoshihide Hayashizaki, Tsukuba (JP)

(73) Assignee: Riken (JP)

( * ) Notice: Subject to any disclaimer, the term of this patent is extended or adjusted under 35 U.S.C. 154(b) by 0 days.

(21) Appl. No.: 09/600,747

(22) PCT Filed: Jan. 22, 1999

(86) PCT No.: PCT/JP99/00223

§ 371 Date: Aug. 29, 2000

§ 102(e) Date: Aug. 29, 2000

(87) PCT Pub. No.: WO99/37808

PCT Pub. Date: Jul. 29, 1999

(30) Foreign Application Priority Data

Jan. 22, 1998 (JP) .................................................. 10-10471

(51) Int. Cl.[7] .............................. C12Q 1/68; C12P 19/34
(52) U.S. Cl. ......................... 435/6; 435/91.1; 435/91.2; 435/91.21; 435/91.5; 435/91.51; 536/23.1; 536/24.33
(58) Field of Search ............................. 435/6, 91.1, 91.2, 435/91.5, 91.51, 91.21; 536/23.1, 24.33

(56) References Cited

U.S. PATENT DOCUMENTS 5,270,184 * 12/1993 Walker et al. ..................... 435/91.2
6,074,824 * 6/2000 Hayashizaki et al. ................ 435/6

* cited by examiner

*Primary Examiner*—Carla J. Myers
*Assistant Examiner*—Alexander H. Spiegler
(74) *Attorney, Agent, or Firm*—Burns, Doane, Swecker & Mathis, L.L.P.

(57) ABSTRACT

A method for sequencing a target DNA fragment in which along with amplification of the target DNA fragment, nucleic acid transcripts are generated using an RNA polymerase and the amplified target DNA fragments are used as templates in the presence of terminators for nucleic acid transcription reaction and the generated nucleic acid transcripts are analyzed, characterized in that the amplification of target DNA fragments and the generation of nucleic acid transcripts are carried out at a constant temperature is disclosed. The amplification of target DNA fragments and the generation of nucleic acid transcripts can be carried out around the room temperature. A DNA sequencing method using a novel method in which without using a thermoresistant RNA polymerase, the amplification of target DNA fragments and generation of nucleic acid transcript can be carried out simultaneously in parallel is provided.

17 Claims, 1 Drawing Sheet

METHOD FOR DETERMINING DNA NUCLEOTIDE SEQUENCE

RELATED FIELDS

The present invention relates to a method for DNA sequencing utilizing the strand displacement amplification method. The present invention relates to a method of DNA sequencing using RNA polymerase in which amplification of a target DNA fragment and preparation of ribonucleotide fragment for DNA sequencing can be performed in parallel without variation of the temperature.

BACKGROUND TECHNOLOGY

Polymerase chain reaction (PCR) is an excellent method, and its field of application increases every year (Randall K. Saiki et al. (1988) Science 239, 487–491). In PCR, it is also possible to amplify DNA fragment starting with just of 1 molecule. A method in which an amplified product of PCR is sequenced without cloning (direct sequencing method) is also useful (Corinne Wong et al. (1988) Nature, 330, 384–386). This method requires neither preparation nor screening of a library, and it is a rapid method enabling to simultaneously obtain sequence information of multiple samples.

Moreover, the inventor introduced a completely novel DNA sequencing method which does not require to remove remaining unreacted primers and 2'deoxyribonucleoside5'triphosphate (2' dNTPs), and which does not require denaturation so that the problem of quick regeneration of PCR products could be obviated [WO96/14434]. This method is a direct sequencing method using RNA polymerase such as T7 RNA polymerase and terminators for RNA transcription reaction (e.g. 3'deoxyribonucleoside5'triphosphate, 3'dNTPs).

The above-mentioned direct transcription sequencing method is performed as described below. RNA polymerase is reacted in a mixture of ribonucleoside5'triphosphates (NTPs) and deoxyribonucleotide(s) (3' dNTP(s)) using DNA amplified by PCR method and the like as a template. In this reaction, ribonucleotides having the bases corresponding to the template DNA sequence are incorporated into a ribonucleotide sequence, termination occurs within corporation of 3'deoxyribonucleotide, and as a result a polynucleotide is synthesized. Resulted polyribonucleotides (nucleic acid transcription products) are separated, and the DNA sequence is determined by analyzing nucleic acid sequence of the separated fraction. Specifically, using florescence labeled 3' dNTP derivatives as a terminator of nucleic acid transcription, nucleic acid sequence can be easily determined by analyzing the label which has been incorporated as a part of the terminator.

By this method, the nucleic acid sequence of PCR-amplified DNA products can be directly used for sequencing without having to remove primers and 2'deoxyribonucleoside5'triphosphates (2' dNTPs). This is because 2' dNTPs do not work as substrates for RNA polymerase. Furthermore, since no denaturation is required, the problem of quick regeneration of the PCR products can be avoided. Therefore the method is extremely powerful.

In the case that a large amount of nucleotide sequence such as the human genome is to be analyzed, a method much more rapid and easier than the existing methods is necessary in order to obtain results in a short time. The above-mentioned direct transcript sequencing method is a relatively rapid method compared to previous sequencing methods utilizing DNA polymerase, however an even more rapid and easier method is necessary. Therefore, it can be thought that a DNA amplification with polymerase chain reaction and a nucleic acid transcript reaction may take place in parallel in the same reaction solution using the above direct transcript sequencing method enabling sequencing rapidly and easily.

However, thepolymerase chain reaction requires an increase or decrease of the temperature of the reaction solution for an amplification of DNA fragments. Therefore, use of thermo-resistant DNA polymerase is required for the polymerase chain reaction. Thus RNA polymerase used for nucleic acid transcript reaction is also required to be thermo-resistant. The above combination method will be possibly performed if a thermo-resistant RNA polymerase having the thermo-resistance similar to that of DNA polymerase would be available. However, at present such thermo-resistant RNA polymerase is not known.

Therefore, an object of the present invention is to provide a method for sequencing DNA in which target DNA amplification and nucleic transcript generation can be operated simultaneously in parallel without use of thermo-resistant RNA polymerase.

SUMMARY OF THE INVENTION

The present invention relates to a method for sequencing a target DNA fragment in which along with amplification of the target DNA fragment, nucleic acid transcripts are generated using an RNA polymerase and the amplified target DNA fragments are used as templates in the presence of terminators for nucleic acid transcription reaction and the generated nucleic acid transcripts are analyzed, characterized in that the amplification of target DNA fragments and the generation of nucleic acid transcripts are carried out at a constant temperature (the first method).

The present invention also relates to a method for sequencing DNA comprising
a step of obtaining nucleic acid transcripts while DNA fragments comprising the target DNA fragment sequence are being amplified
by allowing
(g) a DNA polymerase and
(h) a RNA polymerase to work in the presence of
(a-1) a DNA fragment comprising the target DNA fragment sequence wherein the DNA fragment comprises a sequence accepting formation of a nick and on at least one strand, a promoter sequence for a RNA polymerase,
(b) a primer comprising a primer sequence for one strand of the target DNA fragment and a sequence accepting formation of a nick (hereinafter referred to primer G1)
(c) a primer comprising a primer sequence for the other strand of the target DNA fragment and a sequence accepting formation of a nick (hereinafter referred to primer G2),
provided that at least one of the primers G1 and G2 comprises the promoter sequence for the RNA polymerase,
(d) deoxyribonucleoside-5'-triphosphates comprising dATP, dGTP, dCTP and dTTP or derivatives thereof (hereinafter referred to dNTP derivatives),
(e) ribonucleoside-5'-triphosphates comprising ATP, GTP, CTP and UTP or derivatives thereof (hereinafter referred to NTP derivatives), and
(f) 3'-deoxyribonucleoside-5'-triphosphates comprising 3'dATP, 3'dGTP, 3'dCTP and 3'dUTP or derivatives thereof (hereinafter referred to 3'dNTP derivatives), and by forming a nick at a site of the DNA fragment (a-1) accepting formation of a nick; and a step of separating the resulting nucleic acid transcripts and reading the nucleic acid sequence from the separated fractions (the second method).

The present invention further relates to a method for sequencing a DNA comprising a step in which primer B1 (a primer complementary to one strand of the target DNA fragment), primer B2 (a primer complementary to the other strand of the DNA fragment), primer G1, and primer G2 hybridize to the DNA fragment (provided that the primer B1 hybridizes to a site closer to 5' end of one strand of the DNA fragment than the site recognized by primer G1, and the primer B2 hybridizes to a site closer to 5' end of the other strand of the DNA fragment than the site recognized by primer G2), and a step of obtaining nucleic acid transcripts while DNA fragments comprising the target DNA fragment sequence are being amplified, by allowing (g) a DNA polymerase and (h) a RNA polymerase to work on the target DNA (a-2) obtained from the hybridization in the presence of (b) primer G1, (c) primer G2, (d) dNTP derivatives, (e) NTP derivatives and (f) at least one kind of 3' dNTP derivatives and by forming a nick at a site of the DNA fragment (a-2) accepting formation of a nick; and a step of separating the resulting nucleic acid transcripts and reading the nucleic acid sequence from the separated fractions (The third method).

MODES FOR CARRYING OUT THE INVENTION

Figure 1:
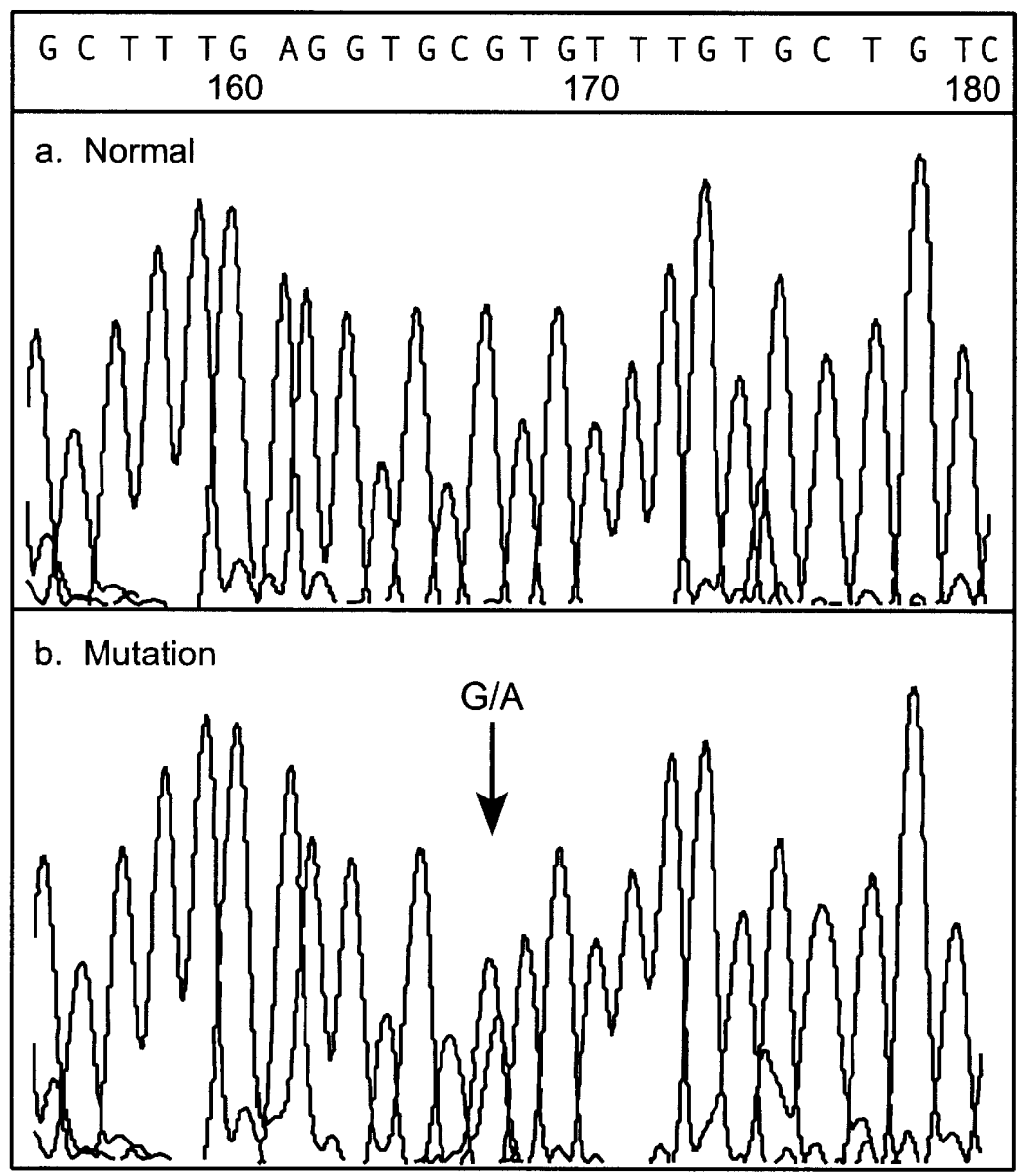
FIG. 1 is an electrogram of nucleic acid obtained from the Example.

Methods of the present invention are briefly composed of a step in which a DNA fragment comprising the target DNA fragment sequence is amplified and nucleic acid transcript products are produced using amplified DNA fragments as a template, and a step in which obtained nucleic acid transcript products are separated and nucleic acid sequence is determined from the separated fraction.

In the first method, along with amplification of a target DNA fragment, nucleic acid products are produced by means of RNA polymerase using the amplified target DNA fragments as a template in the presence of terminators of a nucleic acid transcript reaction, and sequencing the resulting nucleic acid sequence of target DNA fragments by analyzing generated nucleic acid transcripts. This method is characterized in that the amplification of said target DNA fragment and production of nucleic acid transcript are operated at a constant temperature. The "constant temperature" herein means that the reaction temperature is not to intentionally be increased or decreased. Amplification of a target DNA fragment and production of nucleic acid transcripts can be conducted around the room temperature, and the temperature used can be selected considering an optimum temperature of enzymes in use such as RNA polymerase.

The amplification of a target DNA fragment can be carried out by using, for example, the strand displacement amplification (SDA) method. The SDA method is described in Walker et al., Nucleic Acids Research, 1992 Vol.20, No.7, 1691–1696. The SDA method is a method in which the DNA polymerase and restriction enzymes are allowed to work on a target DNA fragment in the presence of substrates of DNA polymerase and primers for the target DNA fragment. The above primers consist of a combination of sense direction and antisense direction, both primers include a sequence in which a nick can be formed by restriction enzymes. Moreover, at least one primer comprises a promoter sequence for RNA polymerase.

In addition, a method of producing nucleic acid transcripts by RNA polymerase utilizing a target DNA fragment as a template in the presence of terminators of a nucleic acid transcript reaction and analyzing the resulting nucleic acid transcripts can be a method in which the nucleic acid transcription reaction is conducted in the presence of substrates for RNA polymerase and labeled terminators, and the analysis of nucleic acid transcripts is carried out by detection of the labels which have been incorporated into the nucleic acid transcripts. Examples of such methods include a direct transcript sequencing method utilizing RNA polymerase such as T7 RNA polymerase and RNA transcript reaction terminators (for example, 3'-deoxyribonucleoside-5'triphosphate, 3' dNTPs) described in WO96/14434.

The second and the third method are embodiments of the first method.

Step of Amplification and Nucleic Transcription

In the second method, a DNA fragment (a-1) comprising a target DNA fragment sequence is used as template of amplification, and this DNA fragment comprises a sequence accepting nick formation and a promoter sequence for RNA polymerase on at least one strand.

In the third method, a target DNA fragment (a-2) hybridized with primer B1, primer B2, primer G1, and primer G2 is used as template for amplification.

The "target DNA fragment" is a fragment to be analyzed for its nucleic acid sequence. There is no special limitation to the kind and length of the target DNA fragment.

The "sequence accepting nick formation" is, for example, "a restriction enzyme site comprising a hemiphosphorothioate site or analogue thereof". The "restriction enzyme site comprising a hemiphosphorothioate site" is that one of the nucleotides of the restriction enzyme site being an αS body (1-thiotriphosphate). If a restriction enzyme reacts at a restriction enzyme site comprising hemiphosphorothioate, the nucleotide complementary to the αs body is cleaved and a nick is introduced (only one side of the strand is cleaved). And, if necessary a sequence of restriction enzyme site can be determined according to the kind of restriction enzyme used for nick formation described below.

"Promoter sequence for RNA polymerase" is a promoter sequence recognized by RNA polymerase used for the nucleic acid transcription reaction described below. The promoter sequence for RNA polymerase is selected according to the kind of RNA polymerase used.

DNA fragment (a-1) comprising a target DNA fragment sequence, a sequence accepting nick formation and a promoter sequence for RNA polymerase can be prepared, for example, by the method described below.

The above sequence is prepared by a method comprising a step of hybridizing the primer B1, primer B2, primer G1 and primer G2 to the DNA fragment, a step where DNA polymerase is allowed to work on the target DNA fragment in the presence of dNTP derivatives. Primer B1 is a primer which binds to one strand of the target DNA sequence, and primer B2 is a primer which binds to the other strand of target DNA sequence, primer G1 is a primer comprising a primer sequence for one strand of target DNA fragment and a sequence accepting nick formation, and primer G2 is a primer comprising a primer sequence for the other strand of the target DNA fragment and a sequence accepting nick formation. Provided that the primer B1 hybridizes at a position closer to the 5'end of one strand of the target DNA fragment than the primer G1, and the primer B2 hybridizes at a position closer to the 5'end of the other strand of the target DNA fragment than the primer G2.

Hybridization of primers to the DNA fragment can be performed by, for example, heat treatment at 95° C. for 4 minutes, followed by slow cooling. The sequences of primer B1 and primer G1 are selected such that primer B1 can hybridize to 5'upstream compared to primer G1. In addition, each primer sequence is selected such that the primers B1 and G1 hybridized to the DNA fragment are separated by a single strand region on the hybridized products. Similarly, as for primer B2 and primer G2, each primer sequence is selected such that primer B2 hybridizes to 5' upstream, and the primers B2 and G2 hybridized to the DNA fragment are separated by a single strand region on the hybridized products. Each primer can be suitably synthesized by conventional methods.

These strands to which the primer B1 and primer G1 or the primer B2 and primer G2 have hybridized can be amplified by the strand displacement amplification method using DNA polymerase in the presence of dNTPs. The strand displacement amplification method is described in Walker et al., Nucleic Acids Research, 1992 vol.20, No.7, 1691–1696. Moreover, in the above amplification, if αS body is utilized for one of dNTP derivatives, a restriction site comprising a hemiphosphorothioate site can be formed. In addition, the selection of the αS body of dNTP derivatives can be suitably determined according to a sequence of restriction site.

In the third method, the target DNA fragment (a-2) hybridized to the primer B1, primer B2, primer G1 and primer G2 is used as a template for amplification. The "target DNA fragment" is the fragment to be analyzed for its nucleic acid sequence. There is no special limitation to the kind and length of the target DNA fragment. The Primer B1, primer B2, primer G1 and primer G2 are as described above, and as for primer B1 and primer G1, the sequences are selected such that primer B1 hybridizes to 5' upstream compared to primer G1. Moreover, each primer sequence is selected such that a single strand region exists between the primers B1 and G1 on the hybridized products. Similarly, as for the primer B2 and primer G2, each primer sequence is selected such that primer B2 hybridizes to 5' upstream compared to primer G2 and a single strand region exists between primer B2 and primer G2 on the hybridized products. Further, each primer can be suitably synthesized by conventional methods. Hybridization of primers to the target DNA fragment can be conducted by, for example, heat treatment at 95° C. for 4 minutes, followed by gradual cooling.

In the third method, a DNA fragment (a-2) comprising the target DNA fragment sequence (provided that this DNA fragment comprising a sequence accepting nick formation and a promoter sequence for RNA polymerase in at least a single strand) is produced by DNA polymerase as described above using the hybridization products as a template in the beginning of amplification and nucleic acid transcript step.

In the amplification and the nucleic acid transcription step, (g) DNA polymerase and (h) RNA polymerase are allowed to work on the (a-1) or (a-2) target DNA fragment in the presence of (b) primer G1, (c) primer G2, (d) dNTP derivatives (provided that, one of dNTP derivatives is αS body), (e) NTP derivatives and (f) at least one of 3'dNTP derivatives, and a nick is formed at a site accepting nick formation on the DNA fragment (a-1) or (a-2). This reaction is conducted at a substantially constant temperature without increasing or decreasing the temperature. However, the reaction temperature is suitably determined based on the optimum temperatures of the each enzyme. Nick formation on DNA fragments (a-1) and/or (a-2) can be performed with restriction enzymes. Some restriction enzymes form a nick by recognizing, for example, a hemiphosphorothioate site locating on a restriction enzyme site. Furthermore, a sequence accepting nick formation can be a restriction enzyme site which comprises a hemiphosphorothioate site or an analogous site thereof, and one of dNTP derivatives used at the time is a αS body or a similar compound.

In the above described reaction system, reactions catalyzed by DNA polymerase, restriction enzymes and RNA polymerase operate in parallel.

The restriction enzyme cleaves a sequence accepting nick formation, for example, a restriction site comprising a hemiphosphorothioate site comprised in (a-1) or (a-2) target DNA fragment and forms a nick at the restriction site of the DNA fragment. It is generally known that when a restriction enzyme, which recognizes a restriction site comprising a hemiphosphorothioate site, works on the restriction site, a nick is formed on a strand complementary to a strand having a hemiphosphorothioate site only on one of strands. In the present invention, primer chains G1 and G2 do not contain hemiphosphorothioate. Thus among restriction sites composed of the primers existing on double strand, only one strand has a hemiphosphorothioate sites, and therefore a nick is formed on such a restriction site. However, even if the same restriction site exists in the target DNA fragment, since sites which do not comprise one of the primer chains have hemiphosphorothioate sites on both of strands, a nick unnecessary for the present purpose will not be formed.

Further, a nick formation activity of restriction enzymes varies depending on the kind of the enzymes, therefore a restriction enzyme used can be selected in view of its activity. HincII, BstBI, AvaI and the like can be used as a restriction enzyme without any limitation. Moreover, suitable restriction enzymes is available from commercial enzymes.

DNA polymerase amplifies a sequence by strand displacement amplification reaction which starts from a nick formed on a DNA fragment by the restriction enzyme and uses as a template the DNA fragment to which a nick has been formed. dNTP derivatives are used as substrates. Furthermore, when a sequence accepting nick formation is a restriction site comprising hemiphosphorothioate, a hemiphosphorothioate site can be formed on such restriction site of the DNA fragment by amplification using as-body as one of dNTP derivatives. αS-bodies of dNTP derivatives are commercially available. Further, based on the sequence of the restriction site, one can select dNTP to become the αs-body.

DNA polymerase used is not specially limited, and can be suitably selected from DNA polymerases which can readily catalyze a strand displacement amplification reaction. Examples of the DNA polymerase include Bst pol, exe klenow and the like, but not limited to these. The DNA polymerases are also commercially available.

RNA polymerase uses a DNA fragment amplified by DNA polymerase as a template, and produces a nucleic acid transcript by using (e) four kinds of NTP derivatives having different bases and (f) at least one kind of 3' dNTP derivative as substrates.

The synthesis of RNA or nucleic acid is terminated by incorporation of 3' dNTP derivatives into the 3' end of the RNA or nucleic acid transcript since the 3' dNTP derivatives lack the 3' hydroxy-residue. As a result, RNA or nucleic acid fragment with different length having 3' dNTP derivatives at 3' ends are produced. Such deoxyribonucleotide-analogues can be obtained for each of the four kinds of 3' dNTP derivatives having different nucleotide. The four kinds of deoxyribonucleotide-analogues can be used to determine the RNA or nucleic acid sequence [Vladimir D. Axelred et al. (1985) Biochemistry Vol. 24, 5716–5723]. 3' dNTP derivatives preferably comprises a label for the purpose of a sequence analysis. Examples of the labels of 3' dNTP derivatives include florescence, radioactive or stable isotopes. 3' dNTP derivatives labeled with a stable isotope are commercially available. Further, labeled 3' dNTP derivatives can be synthesized by using known methods [for example, WO96/14434].

In the above mentioned nucleic acid transcription reaction, it is preferred that the sequence with respect to all (four) kinds of nucleic acids can be determined by only one operation in which a transcription reaction is performed using four different 3' dNTP derivatives having different nucleic acid each are labeled with a different label, the resulting nucleic acid transcription reaction products are separated, and the nucleic acid sequence is determined by analyzing the signals from the different labels of the obtained separated fractions.

Therefore, four kinds of transcription products with different 3' dNTP derivatives at 3' ends can be obtained by four nucleic acid transcription reactions using four different 3' dNTP derivatives. In each of the nucleic acid transcription reactions, any one of 3' dNTP derivatives is used. However, this method is not efficient.

In the second method, a nucleic acid transcription step can be performed by using a DNA fragment (a-1) of which one strand comprises a sequence accepting nick formation and a promoter sequence for RNA polymerase, one of the primer G1 and G2 which comprises a promoter sequence for an RNA polymerase (the promoter sequence is preferably the same as the sequence which is comprised in the DNA fragment (a-1)), and a RNA polymerase which can be activated by the promoter sequence. In this case, the sequence is determined by reading the sequence of only one strand of the target DNA fragment.

It is possible to determine the sequences by reading both strands of the target DNA fragment. In this case, the used DNA fragment (a-1) comprises a sequence accepting nick formation and a promoter sequence for RNA polymerase in both strands. Moreover, primers G1 and G2 each comprising a promoter sequence for RNA polymerase are used. Provided that, the promoter sequence comprised in the primer G1 is identical with one of the promoter sequences comprised in one strand of the double strand DNA fragment (a-1). The promoter sequence comprised in the primer G2 is identical with the other of the promoter sequences comprised in the other strand of the double strand DNA fragment (a-1). In addition, the nucleic acid sequence analysis comprising a step of nucleic acid transcription is performed by using one of two RNA polymerases which is activated by only one of the two promoter sequences. Analysis data with respect to each strand of the target DNA fragment can be obtained by conducting the nucleic acid sequence analysis comprising a step of nucleic acid transcription using different RNA polymerases. The nucleic acid sequence of the target DNA fragment can be determined based on the resulting two kinds of analysis data. In this case, the reading accurateness can be advantageously improved since determination of the nucleic acid sequence is conducted independently with respect to each strand of the target DNA fragment, and the sequence is determined based on the resulting sequences with respect to two strands.

The RNA polymerase can either be a wild-type RNA polymerase or a mutant RNA polymerase. The mutant RNA polymerase is preferably a modified wild-type RNA polymerase of which at least one amino acid has been modified to improve its 3' dNTP derivatives incorporation activity compared to that of the wild type RNA polymerase. The "wild type RNA polymerase" herein includes all RNA polymerase existing in the nature, moreover, it can also be a modified wild type RNA polymerase which has substitution, insertion or deletion of amino acids which are not the modification for obtaining increased activity for incorporating 3'-deoxylibonucleotide or its derivative in comparison with the corresponding wild type RNA polymerase. That is, wild type RNA polymerases artificially modified with a purpose other than that described above are included in the above "wild-type RNA polymerase". It is suitable to make such a substitution, insertion or deletion of amino acids to the extent that the activity of RNA polymerase is maintained.

Examples of the mutant RNA polymerase include mutant T7 RNA polymerases F644Y and L665P/F667Y. The numbers indicate an amino acid number counting from the N terminal of the polymerase protein. For example, F667 means that the amino acid residue No. 667 is F, and F667Y means that the amino acid residue F No. 667 is substituted by Y. These sustain the RNA synthesis activity sufficiently and have an improved ability for incorporating 3' dNTPs. The strong bias observed in the wild-type has been considerably decreased.

Mutant RNA polymerases can be prepared using general recombinant DNA technology. Further, *E. coli* strain pT7RF644Y (DH5 α) and pT7RL665P/F667Y (DH5 α), which produce the mutant T7 RNA polymerase F644Y and L665P/F667Y respectively, were deposited at the National Institute of Bioscience and Human-Technology (NIBH) with international deposition numbers 5998 (FERM-BP-5998) and 5999 (FERM-BP-5999) on Jul. $2^{nd}$, 1997.

A system in which the amplification and nucleic acid transcription reaction of a DNA fragment comprising the target DNA fragment sequence are performed simultaneously in parallel is described above. However, it is possible to sequentially perform a DNA fragment amplification comprising the target DNA fragment sequence using the strand displacement amplification method first, and a nucleic acid transcription reaction using the obtained DNA fragment as a template. However, as described above, it is simple and efficient to simultaneously perform a DNA fragment amplification and nucleic acid transcription reaction in one reaction vessel in parallel.

Separation and Detection of Nucleic Acid Transcript

In the method of the present invention, a nucleic acid transcription product is separated. The separation can be suitably performed by any method which enables the separation of numerous product molecules having different molecular weight, included in the transcription products according to the molecular weight. Examples of such methods include electrophoresis. HPLC can also be used.

Conditions of electrophoresis and the like are not particularly limited and it can be carried out in a conventional manner. The sequence of RNA or nucleic acid can be determined from bands (nucleic acid ladder) provided by subjecting the transcription products to electrophoresis.

RNA or nucleic acid ladders can be read by detecting labels of 3' dNTP derivatives which have been incorporated in the transcription reaction into each fragment. More precisely, a sequence of the transcript can be determined by detecting radioactive or stable isotope atom, or florescence of obtained bands which result from an electrophoresis of labeled transcripts. For the detection of ladders generating radioactivity or stable isotope atom, or florescence, for example, a system used for DNA sequencing can suitably be used.

From the RNA or nucleic acid sequence determined as above, DNA sequence used for the template of transcript can be determined. When a ladder is formed for each nucleic acid, DNA sequence used as a template of the transcription can be determined by integrating the information of RNA or nucleic acid sequence provided from four kinds of ladders. Further, when ladders are formed for two or more nucleic acids (bases) simultaneously (in the case that two or more nucleic acid bands are present in the same ladder), DNA sequence used as a template for the transcription can be determined by integrating the RNA or nucleic acid sequence information obtained from each of the ladders. In particular, when a ladder is simultaneously formed for four kinds of nucleic acids (in the case that four kinds of nucleic acids bands are present in a ladder), DNA sequence used as a template for the transcription can be determined from RNA or nucleic acid sequence information obtained from the ladder.

The method of the present invention is a DNA sequencing method utilizing a novel method which can perform a target DNA amplification and a preparation of nucleic acid transcripts at the same time in parallel. In the present invention, a target DNA amplification and preparation of nucleic acid transcripts, which have been conventionally conducted independently, can be performed simultaneously in parallel, therefore nucleic acid sequencing of DNA can be done more efficiently than the conventional method.

EXAMPLE

The present invention is further illustrated in following example.

A sequencing method of the present invention is used for a specific site of human p53 gene used for diagnosis of mutant cancer and the like.

Material
1) Preparation of Primers

Preparation of primers: four kinds of primers were prepared near p53 exon 8 referring to following references (1) and (2).

Reference (1) Relating to SDA

Walker, G. T., Fraiser, M. S., Schram, J. L., Little, M. C., Nadeau, J. G. and Malinowski, D. P. Nucleic Acids res. 20 (1992) 1691–1696. Strand displacement amplification—an isothermal, in vitro DNA amplification technique.

Walker, G. T., Little, M. C. Nadeau, J. G. and Shank, D. D. Proc. Natl. Acad. Sci. USA 89 (1992) 392–396. Isothermal in vitro amplification of DNA by a restriction enzyme/DNA polymerase system.

Reference (2) Relating to Nucleic Acid Sequence of Human p53

Buchman, L. L. Chumakov, P. M., Ninkina, N. N., Samarina, O. P. and Giorgiev, G. P. Gene 70 (1988) 245–252. A variation in the structure of the protein-coding region of the human p53 gene.

Primer B1: 5'-CCTATCCTGAGTA (13mers, nucleic acid sequence No. 1408–1420) (SEQ ID NO: 1)
Primer B2: 3'-TGATTCAGAACCC (13mers, complement to nucleic acid sequence No. 1664–1676) (SEQ ID NO: 2)
Primer G1: 5'-CGAATCGTTGT<u>CTCGGGGCA TAATACGACTCACTATAGGGCCC AATCTACTGGGAC</u>(SEQ ID NO: 3) (The first underlined site from 5'end: a restriction site; the second underlined site: promoter site for T7 RNA polymerase; the third underlined site: 13 nucleic acids; complement to p53 nucleic acid sequence No. 1227–1338)
Primer G2: 3'-<u>TCTTATAAAGTGG GGGCTCTTCAGACCTCGCCTTAGC</u> (SEQ ID NO: 4) (The first underlined site from 3'end: 13 nucleic acids: complement to p53 nucleic acid sequence No. 1643–1655, the second underlined site: restriction site)

2) Enzyme

Restriction enzyme BsoBI: purchased from New England Biolab. This enzyme cleaves C/PyCGpuG sequence. DNA polymerase (Bst po1): purchased from Epicentre. T7 RNA polymerase (mutant, F644Y) : mutant T7 RNA polymerase in which F (phenylalanine) residue No. 667 was replaced by Y (tyrosine) residue wild type T7 RNA polymerase.

3) DNA

Human placental DNA and Ht-29 cell line from human large intestine cancer (obtained from ATCC) are used. The p53 DNA of said cancer cell line is known to contain a replacement of its amino acid R by H at No. 273 of exon site 8 (G→A replacement).

See Reference (3) Murakami, Y., Hayashi, K., Hirhashi, S. and Sekiya, T. Cancer Res. 51 (1991) 5520–5525. Aberration of the tumor suppressor p53 and retinoblastoma genes in human hepatocellular carcinomas.

Murakami, Y., Hayashi, K. and Sekiya, T. Cancer Res. 51 (1991) 3356–3361. Detection of aberrations of the p53 alleles and the gene transcript in human tumor cell lines by single-strand conformation polymorphism analysis.

Method
(1) The following materials were mixed and modified at 95° C. for 4 minutes, and then primer annealing was performed at 37° C. 15 for one minute.
0.5 µg/ml human placental DNA or human cancer cell line DNA . . . 1 µl
Each primer G1 and G2 (10 µM) . . . 1 µl
Each primer B1 and B2 (1 µM) . . . 1 µl
dGTP, dATP, dTTP (2 mM each) . . . 2 µl
d αSCTP (10 mM) . . . 2 µl
10×buffer * . . . 2 µl
GTP, ATP, UTP, CTP (2 mM each) . . . 5 µl
Water . . . 1 µl
four color florescence labeled nucleotide mixture ** . . . 1 µl
(notes: * 500 mM NaCl, 100 mM Tris-HCl (pH 7.5), 100 mM MgCl$_2$, 10 mM DTT solution; ** a mixed solution of R11C-3'dGTP 1 µM, R6G-3'dATP 1 µM, ROX-3'dCTP 50 µM, TMR-3'dUTP 12.5 µM; R11C-3'dGTP, R6G-3'dATP, ROX-3'dCTP and TMR-3'dUTP are florescence labeled 3'dNTP)
(2) The following materials were added to the mixture of (1) to give a final volume of 20 µl, and allowed to react at 45° C. for 2 hours.
Restriction enzyme BsoBI (10 units/µl) . . . 1 µl
DNA polymerase (Bst po1) 5 units/µl . . . 2 µl
T7 RNA polymerase (F644Y) 25 units/µl . . . 1 µl
(3) The reaction solution is analyzed by electrophoresis for sequencing.

FIG. 1 shows an electrogram of nucleic acid sequences which correspond to a part of p53 exon of human placental DNA (upper) and human cancer cell line HT29 DNA (lower). As seen from the figure, in the upper figure, amino acid at 273 is R(CGT) , on the other hand, in the lower figure, half of them are the amino acid H(CAT).

In the present invention, nucleic acid sequencing can be performed through a DNA amplification in the same cube at the same temperature after only once heat denaturation.

What is claimed is:

1. A method for sequencing a target DNA fragment comprising amplifying the target DNA fragment, generating nucleic acid transcripts from the target DNA fragment using an RNA polymerase in the presence of terminators for nucleic acid transcription reactions, and determining the sequence of said nucleic acid transcripts, wherein said amplifying and generating are carried out at a constant temperature.

2. The method according to claim 1, wherein the amplification of target DNA fragments and the generation of nucleic acid transcripts are carried out at around room temperature.

3. The method according to claim 1, wherein the amplification of target DNA fragments is carried out by the strand displacement amplification method.

4. The method according to claim 3, wherein the strand displacement amplification method comprises
combining a DNA polymerase and a restriction enzyme with the DNA fragment in the presence of substrates for the DNA polymerase and two primers for the target DNA fragment wherein the primers comprise a restriction enzyme recognition sequence.

5. The method according to claim 4 wherein one or both of the primers comprises a promoter sequence for the RNA polymerase in addition to the restriction enzyme recognition sequence.

6. The method according to claim 1, wherein the nucleic acid transcription is carried out in the presence of substrates for the RNA polymerase and labeled terminators, wherein the step of determining the sequence of said nucleic acid transcripts is carried out by detecting.

7. A method for sequencing DNA comprising
obtaining nucleic acid transcripts while DNA fragments comprising a target DNA fragment sequence are being amplified, by combining a DNA polymerase and a RNA polymerase with
a DNA fragment (a-1) comprising the target DNA fragment sequence
wherein the DNA fragment (a-1) comprises a sequence accepting formation of a nick and on at least one strand, a promoter sequence for a RNA polymerase,
a primer (G1) comprising
a primer sequence for one strand of the target DNA fragment and a restriction enzyme recognition sequence,
a primer (G2) comprising
a primer sequence for the other strand of the target DNA fragment and a sequence accepting formation of a nick,
provided that at least one of the primers G1 and G2 comprises the promoter sequence for the RNA polymerase,
deoxyribonucleoside-5' triphosphates comprising dATP, dGTP, dCTP and dTTP or derivatives thereof,
ribonucleoside-5' triphosphates comprising ATP, GTP, CTP and UTP or derivatives thereof, and
3' deoxyribonucleoside-5' triphosphates comprising 3' ATP, 3' GTP, 3' CTP and 3' UTP or derivatives thereof,
forming a nick at a site of the DNA fragment (a-1) accepting formation of a nick;
separating the nucleic transcripts; and
determining the nucleic acid sequence of said nucleic acid transcript.

8. A method according to claim 7, wherein the target DNA fragment (a-1) is prepared by a method comprising hybridizing
a primer (B1) for one strand of the target DNA fragment,
a primer (B2) for the other strand of the target DNA fragment,
a primer G1 and
a primer G2
to the DNA fragment in the presence of dNTP derivatives, wherein
primer B1 hybridizes to a site closer to 5' end of one strand of the DNA fragment than the site recognized by primer G1, and
primer B2 hybridizes to a site closer to 5' end of the other strand of the DNA fragment than the site recognized by primer G2, and
combining a DNA polymerase with the DNA fragment.

9. A method according to claim 7, wherein
one strand of the target DNA fragment (a-1) comprises restriction enzyme recognition sequence and
a promoter sequence for RNA polymerase,
one of the primers G1 and G2 comprises
a promoter sequence for the RNA polymerase,
wherein this promoter sequence has the same sequence as that comprised in the DNA fragment (a-1), and
the nucleic acid transcription is carried out using an RNA polymerase, wherein the activity of the RNA polymerase is initiated by the promoter sequence.

10. A method according to claim 7, wherein
both strands of the DNA fragment (a-1) comprise restriction enzyme recognition sequence and
a promoter sequence for an RNA polymerase,
each of the primers G1 and G2 comprises
a promoter sequence for RNA polymerase,
wherein the promoter sequence comprised in the primer G1 has the same sequence as one of the promoter sequences comprised in the DNA fragment (a-1),
the promoter sequence comprised in the primer G2 has the same sequence as the other of the promoter sequences comprised in the DNA fragment wherein,
wherein the step of determining the nucleic acid sequence comprises determining the sequence of both strands of the DNA fragment (a-1) independently using two types of RNA polymerase, wherein each RNA polymerase only recognizes one of the two promoter sequences.

11. A method of target DNA sequencing comprising
hybridizing primers B1, B2, G1, and G2 to a DNA fragment (a-1) comprising a target DNA fragment, to produce a DNA fragment (a-2);
obtaining nucleic acid transcripts, while simultaneously amplifying DNA fragments (A-2) comprising the target DNA fragment and performing an extension reaction, by combining
a DNA polymerase and a RNA polymerase
a DNA fragment (a-2)
the primer B1,
the primer G2,
dNTP derivatives,
NTP derivatives and
at least one kind of 3' dNTP derivatives, and
forming a nick at a site of the DNA fragment (a-2) restriction enzyme recognition sequence;

separating the nucleic acid transcripts and determining the nucleic acid sequence of said nucleic acid transcripts.

12. A method according to claim 7, wherein the nick formed on the DNA fragment (a-1) is formed using a restriction enzyme.

13. A method according to claim 7, wherein the restriction enzyme recognition sequence is a restriction site comprising a hemiphosphorothioate site or an analogous site thereof, and one of the dNTP derivatives is an αS derivative or an analogue thereof.

14. A method according to claim 7, wherein the obtaining of nucleic acid transcripts and the amplification of DNA fragment (a-2) are carried out at a substantially constant temperature.

15. A method according to claim 7, wherein the 3' dNTP derivatives are labeled.

16. A method according to claim 15, wherein the label is a fluorescent substance, or a radioactive or stable isotope element.

17. A method according to claim 7, wherein four types of 3' NTP derivatives different in bases and bearing different labels from each other are used for the nucleic acid transcription reaction, and the nucleic transcripts are separated from one another and a nucleic acid sequence is determined from signals obtained from the labels of the separated nucleic acid transcripts.

* * * * *

SEQUENCE LISTING

<160> NUMBER OF SEQ ID NOS: 4

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: 5' primer
      B1; 13mers complementary to nucleic acids 1408-1420 of
      human p53 gene

<400> SEQUENCE: 1
cctatcctga gta                                                          13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: 3' primer
      B2; 13 mers complementary to nucleic acids 1664-1676
      of p53 human gene

<400> SEQUENCE: 2
cccaagactt agt                                                          13

<210> SEQ ID NO 3
<211> LENGTH: 56
<212> TYPE: DNA
<213> ORGANISM: Artificial Sequence
<220> FEATURE:
<221> NAME/KEY: promoter
<222> LOCATION: (21)..(40)
<223> OTHER INFORMATION: promoter site for T7 RNA polymerase
<223> OTHER INFORMATION: Description of Artificial Sequence: 5' primer
      G1;
<221> NAME/KEY: misc_feature
<222> LOCATION: (12)..(17)
<223> OTHER INFORMATION: restriction site
<221> NAME/KEY: misc_feature
<222> LOCATION: (44)..(56)
<223> OTHER INFORMATION: sequence complementary to nucleic acid sequence
      1227-1338 of human p53 gene

<400> SEQUENCE: 3
cgaatcgttg tctcggggca taatacgact cactataggg cccaatctac tgggac          56

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: 3' primer
      G2
<221> NAME/KEY: misc_feature
<222> LOCATION: (19)..(24)
<223> OTHER INFORMATION: restriction site
<221> NAME/KEY: misc_feature
<222> LOCATION: (25)..(37)
<223> OTHER INFORMATION: sequence complementary to nucleic acid sequence
      1643-1655 of human p53 gene

<400> SEQUENCE: 4
cgattccgct ccagacttct cggggtgaa atattct                                 37